(12) United States Patent
Von Bahr

(10) Patent No.: US 6,186,983 B1
(45) Date of Patent: Feb. 13, 2001

(54) BODY FLUID ANALYSIS SYSTEM EMPLOYING A SENSOR AND METHOD FOR FLUSHING AND SINGLE-POINT CALIBRATION OF THE SENSOR

(75) Inventor: Pontus Von Bahr, Stockholm (SE)

(73) Assignee: Siemens Elema AB, Solna (SE)

( * ) Notice: Under 35 U.S.C. 154(b), the term of this patent shall be extended for 0 days.

(21) Appl. No.: 09/109,387

(22) Filed: Jul. 2, 1998

(30) Foreign Application Priority Data

Jul. 17, 1997 (SE) ................................................. 9702738

(51) Int. Cl.[7] .................................................. A61M 1/00
(52) U.S. Cl. ............................................ 604/151; 422/68.1
(58) Field of Search .................................. 604/4–6, 8–9, 604/131, 151, 246–249, 250

(56) References Cited

U.S. PATENT DOCUMENTS

| | | |
|---|---|---|
| 4,608,996 | 9/1986 | Brown . |
| 4,786,394 * | 11/1988 | Enzer et al. .......................... 204/401 |
| 5,057,278 | 10/1991 | Maxwell et al. . |
| 5,165,406 | 11/1992 | Wong . |
| 5,781,284 * | 7/1998 | Infante .................................. 356/73 |

* cited by examiner

*Primary Examiner*—Sharon Kennedy
*Assistant Examiner*—Catherine Serke
(74) *Attorney, Agent, or Firm*—Schiff Hardin & Waite

(57) ABSTRACT

In a body fluid analysis system having a sensor and a method for flushing and single-point calibration of the sensor, a container holding at least one flushing liquid has a first tube connected thereto at a first point and at a second point to form a closed system. The sensor is connected to the first tube, and to a second tube for connection to a patient. A pump is connected to the first tube between the container and the sensor.

14 Claims, 2 Drawing Sheets

BODY FLUID ANALYSIS SYSTEM EMPLOYING A SENSOR AND METHOD FOR FLUSHING AND SINGLE-POINT CALIBRATION OF THE SENSOR

BACKGROUND OF THE INVENTION

1. Field of the Invention

The present invention is directed to a body fluid analysis system for extracorporeal body fluid analysis with a sensor arrangement. The present invention also relates to a method for flushing and single-point calibration of a sensor arrangement in a closed, body fluid analysis system.

2. Description of the Prior Art

In e.g. extracorporeal analysis of blood with known systems for continuous or semi-continuous blood analyses via a venous or arterial catheter, the heart or an external pump pumps the blood to a sensor outside the body. After the blood analysis, performed by the sensor, the blood is returned to the body when a flushing liquid is pumped in the opposite direction. After a large part of the blood has been pumped back to the patient, the sensor is flushed with additional flushing liquid to remove any residual blood. This flushing liquid can either be infused into the patient or collected in a special bag. When flushing has been concluded, the flushing liquid, which is then in contact with the sensor, is sometimes used for calibration.

Instability and a short operating life are the main disadvantages of these known systems for blood analysis.

The number of pumps and the number of bags/containers employed by these known systems are additional disadvantages.

SUMMARY OF THE INVENTION

An object of the present invention is to provide a body fluid analysis system, and a method for flushing and single-pointy calibration of the sensor of such a system, wherein the aforementioned problems are avoided.

The above object is achieved in a body fluid analysis system according to the present invention having a container, holding at least one flushing liquid, and a first tube connected to the container at a first point and at a second point to form a closed system. The sensor is connected to the first tube, and to a second tube for connection to a patient. The body fluid analysis system also has a pump connected to the first tube between the first point and the sensor.

One advantage of the body fluid analysis system according to the present invention is that it can be realized at low cost. The system is also easy to operate. An additional advantage is that the system only needs one pump and one container. Moreover, the body fluid analysis system according to the present invention is stable and has a long operating life.

In an embodiment the body fluid analysis system can also include a valve, connected to the first tube between the second point and the sensor, the pump and valve being connected to the first tube on opposite sides of the sensor.

It is advantageous to operate the body fluid analysis system with higher-than-ambient pressure in the container.

In a further embodiment of the body fluid analysis system, the valve is arranged by the sensor and is also connected to the second tube.

The flow resistance in the two tubes can be optimized by the choice of appropriate tube diameters and/or chokes using the valve.

A filter arrangement for filtering out bacteria can be connected to the first tube between the pump and sensor.

The body fluid analysis system can also include an analysis unit, connected to the container, for monitoring contamination of the flushing liquid(s).

The analysis unit can be a spectral analysis unit or an absorption analysis unit.

The body fluid analysis system additionally can contain an indication arrangement, connected to the analysis unit, for indicating if contamination of the flushing liquid(s) exceeds a redetermined level.

A method according to the present invention for flushing and single-point calibration of a sensor in a closed, body fluid analysis system as described above has the following steps. Body fluid is pumped to the sensor. The body fluid is analyzed using the sensor. Flushing liquid is pumped from a container through the sensor in order to flush the sensor. Flushing liquid is collected in the container after the sensor is flushed.

The method additionally can include the following steps. A valve is closed at the same time as the pump pumps fluid toward the container so as to direct body fluid to the sensor. The valve is kept closed, and the pump is inactive while the sensor analyzes body fluid. The valve is still kept closed at the same time as the pump pumps fluid toward the sensor in order to return the body fluid to the body fluid source. The valve is opened while the pump pumps fluid toward the sensor in order to pump flushing liquid through the sensor.

The method additionally can include the step of filtering out bacteria either in the body fluid or flushing liquid.

The method additionally can include the step of, after the flushing stage, using the flushing liquid for single-point calibration of the sensor.

DESCRIPTION OF THE PREFERRED EMBODIMENTS

Figure 1:
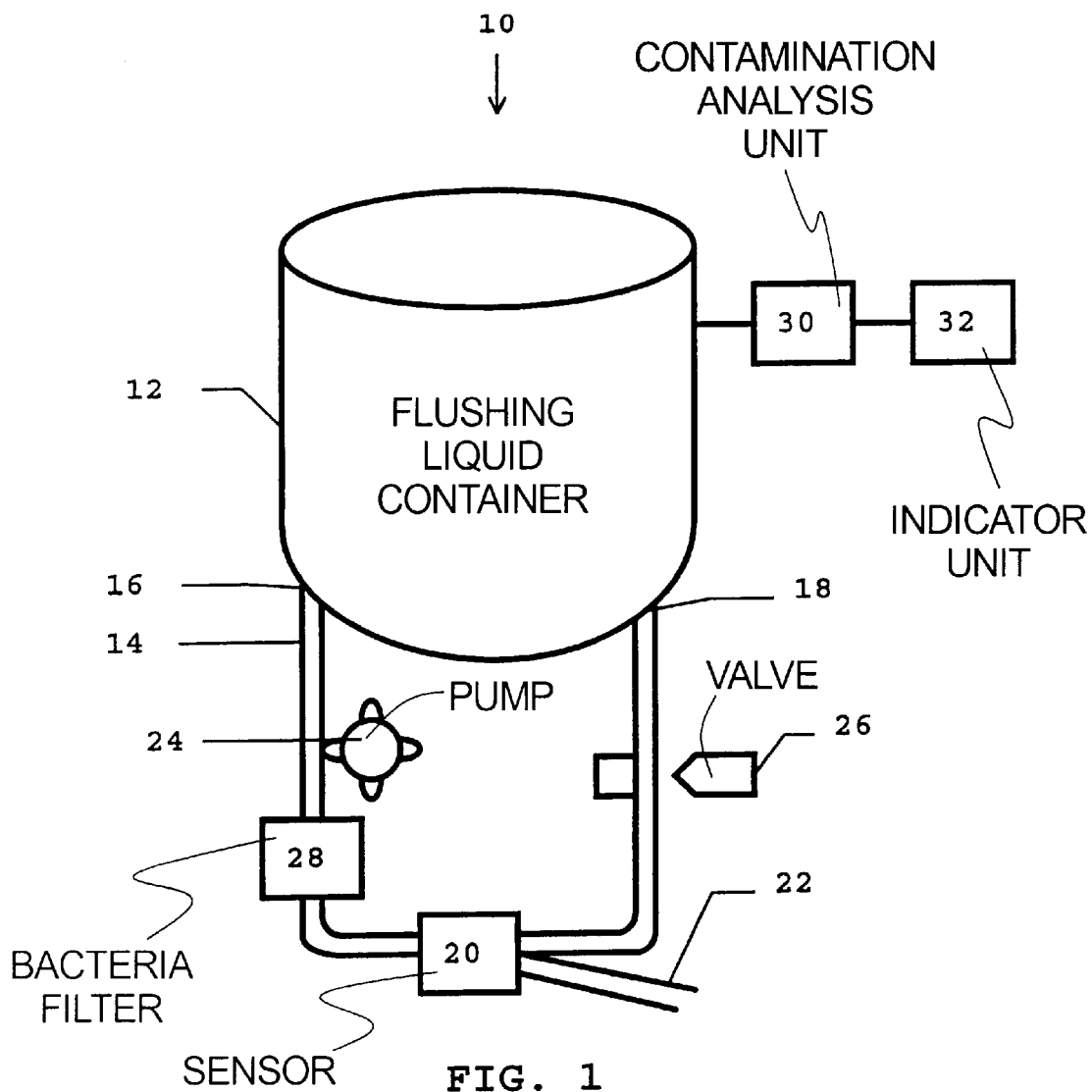
FIG. 1 shows a body fluid analysis system according to the 25 present invention.

FIG. 1 shows a body fluid analysis system 10 according to the present invention for extracorporeal body fluid analysis. This body fluid analysis system 10 is preferably used for blood analyses and will henceforth be referred to as a blood analysis system, even though other body fluids can be analyzed with this system. The blood analysis system 10 includes a container 12 holding at least one flushing liquid. The blood analysis system also includes a first tube 14, connected to the container 12 at two different points, i.e. a first point 16 and a second point 18. The connection points 16 and 18 are arranged so that recirculation develops in the system. These points 16 and 18 are therefore separated at a specific distance from each other to keep them from opening to the same point in the container 12. The container 12 and the first tube 14 accordingly form a closed system.

The blood analysis system 10 also has a sensor 20, connected to the first tube 14, and to a second tube 22. The second tube 22 connects the system 10 to a patient's circulatory system via a venous or arterial catheter (not shown). The blood analysis system 10 also has a pump 24, connected to the first tube 14 between the container 12 and the sensor 20, and a valve 26, connected to the first tube 14 between the container and the sensor 20. As FIG. 1 shows, the pump 24 and the valve 26 are connected to the first tube 14 on either side of the sensor 20. The pump 24 is a double-action pump, i.e. it is able to pump in both directions. The valve 26 can be any kind of ON/OFF valve or the equivalent. The blood analysis system 10 also can include a filter 28, connected to the first tube 14 between the pump 24 and the sensor 20, for filtering out bacteria in blood or flushing liquid(s) respectively. The blood analysis system 10 shown in FIG. 1 operates with above-ambient pressure in the container 12. FIG. 1 schematically depicts an analysis unit 30, connected to the container 12, for analyzing the level of contamination in the flushing liquid(s). This analysis unit 30 can be of e.g. a spectral analysis unit or an absorption analysis unit. An indication unit 32 is, in turn, connected to the analysis unit 30 in order to indicate if and when contamination of the flushing liquid(s) exceeds a predetermined level. The indication can be of e.g. an acoustic or optical signal or a combination thereof. When the indication unit 32 indicates that contamination of the flushing liquid(s) exceeds the predetermined level, the entire container 12 is replaced with a new container, or the flushing liquid(s) in the container 12 is/are replaced.

With regard to contamination, it should be noted that only traces of residual blood can be carried to the container 12, so the same flushing liquid can be used for a long time.

In one version of the body fluid analysis system 10 shown in 15 FIG. 1, the valve 26 is not employed, and the system's container 12 does not utilize above-ambient pressure. If the pump 24 stops or the pump 24 starts pumping in reverse (toward the point 16), arterial pressure will force blood up into the sensor 20 for a predetermined period of time. The pump 24 will then pump forcefully in the opposite direction (toward the point 18), the pressure then generated exceeding arterial pressure, whereupon blood and flushing liquid are carried both to the patient and through the point 18 to the container 12.

A version with an ON/OFF valve on the catheter is also possible. When the valve is open and the pump operates, some of the flushing liquid flows through the catheter. The sensor is flushed when the valve is closed and the pump operates. When the valve is open and the pump is inactive, the heart pumps blood through the sensor. This naturally assumes that there is no positive pressure in the container.

The container 12 can either be flexible and empty of gas or hold just enough air to allow the volume of liquid to increase somewhat without any adverse effects. A gas-tight container 12 is needed for blood gas analysis, of course, so the volume of gas ($CO_2$ in particular) remains constant.

Figure 2:
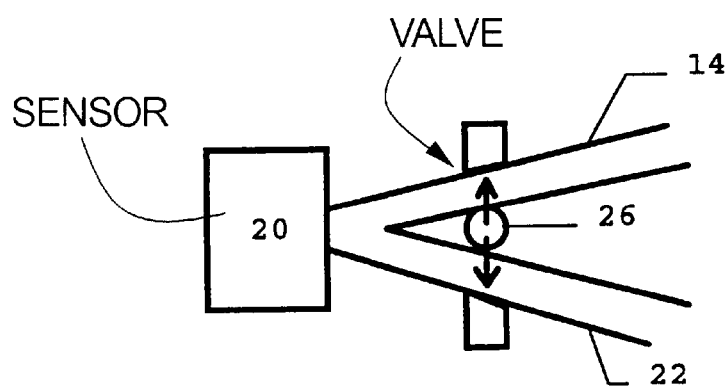
FIG. 2 is a schematic view of an alternative embodiment of the valve in the body fluid analysis system shown in FIG. 1.

FIG. 2 is a schematic view of an alternative embodiment of and location for the valve in the blood analysis system 10 shown in FIG. 1. FIG. 2 only shows the sensor 20, the first tube 14 and the second tube 22 in the blood analysis system 10, in addition to the valve 26'. As FIG. 2 shows, the valve 26' is arranged by the sensor 20 and is connected to and acts on both the first tube 14 and the second tube 22. As FIG. 2 schematically depicts, the valve 26' is able to close either of the tubes 14 or 22, leaving the unclosed tube open.

Figure 3:
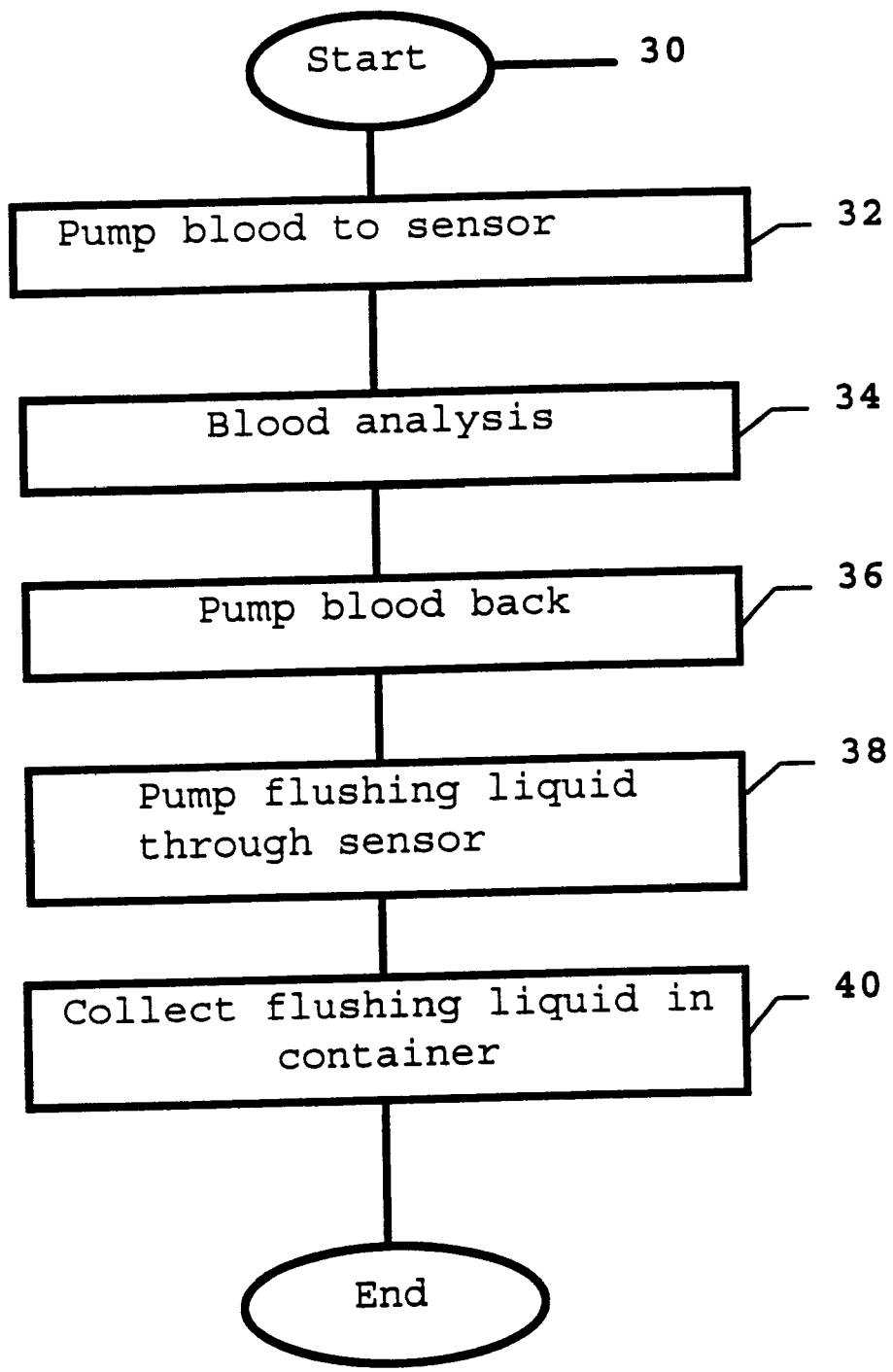
FIG. 3 is a flow chart depicting a method, according to the 30 invention, for flushing and single-point calibration of a sensor in a closed, body fluid analysis system.

FIG. 3 is a flowchart showing a method according to the invention, for flushing and single-point calibration of a sensor body in a closed, body fluid analysis system, e.g. devised according to FIG. 1. The method will be described below for blood, according to the description in FIG. 1, but any other body fluid can be substituted for blood. The method starts at block 30. A pump at block 32 pumps blood to the sensor. The sensor performs a blood analysis at block 34. The pump then pumps the blood at block 36 back to the blood source, i.e. the patient. At block 38, the pump pumps flushing liquid from a container through the sensor in order to flush the sensor. After the sensor has been flushed at block 40, flushing liquid is collected in the container. The method then concludes at block 42. Since the flow of flushing liquid is to and from the same container, the flushing liquid, which is initially sterile, becomes increasingly contaminated, but cleaning is still sufficient if the volume of the container is large enough.

The method according to the invention also can include the following steps.

A valve can be closed at the same time the pump operates in a pumping direction toward the container in order to pump blood to the sensor. The valve is then closed and the pump is inactive while the sensor performs the blood analysis. The valve is then closed at the same time as the pump operates in a pumping direction toward the sensor in order to return blood to the blood source. The valve is then opened at the same time as the pump pumps toward the sensor in order to pump flushing liquid through the sensor. In addition, a filter can filter bacteria out of the blood and flushing liquid respectively. After the flushing step, the flushing liquid is used for single-point calibration of the sensor.

The above description of the method according to the present invention is also a description of the function of the blood analysis system shown in FIG. 1.

Although modifications and changes may be suggested by those skilled in the art, it is the intention of the inventor to embody within the patent warranted hereon all changes and modifications as reasonably and properly come within the scope of his contribution to the art.

I claim as my invention:

1. A body fluid analysis system for extracorporeal body fluid analysis comprising:
    a body fluid analysis sensor;
    a container containing a flushing liquid;
    a first tube connected to said container at a first point and at a second point, spaced from said first point, to form a closed system, said sensor being connected to said first tube;
    a second tube connected to said sensor and adapted for connection to a body fluid source to transfer body fluid between said sensor and said body fluid source; and
    a pump connected to said first tube between said first point and said sensor for pumping flushing liquid and body fluid to and from said sensor and for pumping the flushing liquid to and from said container.

2. The body fluid analysis system as claimed in claim 1 further comprising a valve disposed to interact with said first tube between said second point and said sensor to open and close said first tube, said pump and said valve being disposed respectively on opposite sides of said sensor.

3. The body fluid analysis system as claimed in claim 2 wherein said container has an above-ambient pressure therein.

4. The body fluid analysis system as claimed in claim 2 wherein said valve is also connected to said second tube for opening and closing said second tube.

5. The body fluid analysis system as claimed in claim 2 wherein said first tube has a first tube diameter and wherein said second tube has a second tube diameter, and wherein flow resistance in said first and second tubes is optimized by said first tube diameter and said second tube diameter and said valve.

6. The body fluid analysis system as claimed in claim 1 further comprising a filter connected in said first tube between said pump and said sensor, said filter filtering bacteria out of liquid in said first tube.

7. The body fluid analysis system as claimed in claim 1 further comprising analysis means disposed in said container and interacting with said flushing liquid in said container for monitoring contamination of said flushing liquid.

8. The body fluid analysis system as claimed in claim 7 wherein said analysis means comprises means for spectrally analyzing said flushing liquid.

9. The body fluid analysis system as claimed in claim 7 wherein said analysis means comprises means for conducting an absorption analysis of said flushing liquid.

10. A body fluid analysis system as claimed in claim 7 further comprising an indicator connected to said analysis means which indicates when contamination of said flushing liquid in said container exceeds a predetermined level.

11. A method for flushing and single-point calibration of a sensor in a closed, extracorporeal body fluid analysis system, comprising the steps of:

containing a flushing liquid in a container;

connecting a first tube to said container at a first point and at a second point, spaced from said first point, to form a closed system, said first tube having a fluid flow path associated therewith;

disposing a sensor in said fluid flow path of said first tube;

connecting a second tube between said sensor and a body fluid source for exchanging body fluid between said sensor and said body fluid source;

disposing a pump in said first tube between said first point and said sensor;

providing body fluid from said body fluid source to said sensor;

using said sensor to analyze said body fluid;

operating said pump to pump said body fluid from said sensor to said body fluid source;

operating said pump to pump flushing liquid from said container through said sensor for flushing said sensor; and collecting flushing liquid in said container after passage through said sensor.

12. The method as claimed in claim 11 wherein the step of providing body fluid from said body fluid source to said sensor comprises operating said pump to pump body fluid from said body fluid source to said sensor, and said method comprising the additional steps of:

providing a valve arrangement interacting with said first tube and said second tube;

closing said valve arrangement while operating said pump to pump fluid toward said container for pumping said body fluid to said sensor from said body fluid source;

closing said valve arrangement and maintaining said pump inactive while said sensor performs said body fluid analysis;

closing said valve arrangement while operating said pump for pumping in a direction toward said sensor to pump said body fluid back to said body fluid source; and opening said valve arrangement while operating said pump to pump toward said sensor for pumping flushing liquid from said container through said sensor.

13. The method as claimed in claim 11 comprising the additional step of:

filtering bacteria out of said body fluid and filtering bacteria out of said flushing liquid, respectively.

14. The method as claimed in claim 11 comprising the additional step of:

performing a single-point calibration of said sensor using said flushing liquid after flushing said sensor with said flushing liquid.

* * * * *